(12) United States Patent
Cunningham et al.

(10) Patent No.: US 8,282,634 B2
(45) Date of Patent: Oct. 9, 2012

(54) APPARATUS, SYSTEM, AND METHOD FOR PERFORMING AN ELECTROSURGICAL PROCEDURE

(75) Inventors: James S. Cunningham, Boulder, CO (US); James D. Allen, IV, Broomfield, CO (US); Glenn A. Horner, Boulder, CO (US)

(73) Assignee: TYCO Healthcare Group LP, Mansfield, MA (US)

( * ) Notice: Subject to any disclaimer, the term of this patent is extended or adjusted under 35 U.S.C. 154(b) by 680 days.

(21) Appl. No.: 12/353,474

(22) Filed: Jan. 14, 2009

(65) Prior Publication Data

US 2010/0179547 A1 Jul. 15, 2010

(51) Int. Cl.
*A61B 18/18* (2006.01)
*A61B 18/04* (2006.01)
*A61B 17/00* (2006.01)

(52) U.S. Cl. ............... 606/50; 606/32; 606/45; 606/208

(58) Field of Classification Search .................... 606/32, 606/45, 50–52, 205–211
See application file for complete search history.

(56) References Cited

U.S. PATENT DOCUMENTS

| | | | |
|---|---|---|---|
| 4,074,718 A | 2/1978 | Morrison, Jr. | |
| 5,391,166 A | 2/1995 | Eggers | |
| 5,396,900 A | 3/1995 | Slater et al. | |
| 5,460,629 A | 10/1995 | Shlain et al. | |
| 5,514,134 A | 5/1996 | Rydell et al. | |
| 5,540,685 A | 7/1996 | Parins et al. | |
| 6,090,107 A | 7/2000 | Borgmeier et al. | |
| 6,193,718 B1 | 2/2001 | Kortenbach et al. | |
| 6,228,083 B1 | 5/2001 | Lands et al. | |
| 6,451,018 B1 | 9/2002 | Lands et al. | |
| 7,195,631 B2* | 3/2007 | Dumbauld | 606/51 |
| 7,318,823 B2 | 1/2008 | Sharps et al. | |
| 2002/0099375 A1* | 7/2002 | Hess et al. | 606/51 |
| 2008/0033428 A1* | 2/2008 | Artale et al. | 606/51 |
| 2008/0215051 A1 | 9/2008 | Buysse et al. | |
| 2010/0094287 A1* | 4/2010 | Cunningham et al. | 606/51 |

FOREIGN PATENT DOCUMENTS

| | | |
|---|---|---|
| CA | 2104423 | 2/1994 |
| DE | 2415263 | 10/1975 |
| DE | 2514501 | 10/1976 |

(Continued)

OTHER PUBLICATIONS

U.S. Appl. No. 12/336,970, filed Dec. 17, 2008.

(Continued)

*Primary Examiner* — Nicholas Lucchesi
*Assistant Examiner* — Rebecca E Eisenberg (57) ABSTRACT

A bipolar forceps is provided. The bipolar forceps includes a housing having a shaft including an electrically conductive distal end. A drive assembly is operable to reciprocate an actuation tube within the shaft. A portion of the actuation tube is electrically conductive. An end effector assembly operatively connects to the shaft and includes a pair of first and second jaw members biased in an open configuration. The first and second jaw members are pivotable about a living hinge. Distal reciprocation of the actuation tube causes each of the jaw members towards one another about the living hinge. One of the jaw members is in electrical communication with the distal end of the shaft and the other jaw member is in selective electrical communication with a distal end of the actuation tube such that when the jaw members are in a closed configuration a closed loop electrical circuit is formed.

8 Claims, 4 Drawing Sheets

FOREIGN PATENT DOCUMENTS

| | | |
|---|---|---|
| DE | 2627679 | 1/1977 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 29616210 | 1/1997 |
| DE | 19608716 | 4/1997 |
| DE | 19751106 | 5/1998 |
| DE | 19751108 | 5/1999 |
| DE | 19738457 | 1/2009 |
| EP | 1159926 | 12/2001 |
| GB | 623316 | 5/1949 |
| GB | 1490585 | 11/1977 |
| GB | 2214430 A | 6/1989 |
| GB | 2213416 A | 8/1989 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |

OTHER PUBLICATIONS

U.S. Appl. No. 12/399,614, filed Mar. 6, 2009.
U.S. Appl. No. 12/195,624, filed Aug. 21, 2008.
U.S. Appl. No. 12/367,791, filed Feb. 9, 2009.
U.S. Appl. No. 12/361,367, filed Jan. 28, 2009.
U.S. Appl. No. 12/361,375, filed Jan. 28, 2009.
U.S. Appl. No. 12/400,901, filed Mar. 10, 2009.
U.S. Appl. No. 12/176,679, filed Jul. 21, 2008.
U.S. Appl. No. 12/237,515, filed Sep. 25, 2008.
U.S. Appl. No. 12/204,976, filed Sep. 5, 2008.
U.S. Appl. No. 12/192,170, filed Aug. 15, 2008.
U.S. Appl. No. 12/233,157, filed Sep. 18, 2008.
U.S. Appl. No. 12/237,582, filed Sep. 25, 2008.
U.S. Appl. No. 12/210,598, filed Sep. 15, 2008.
U.S. Appl. No. 12/200,154, filed Aug. 28, 2008.
U.S. Appl. No. 12/211,205, filed Sep. 16, 2008.
U.S. Appl. No. 12/244,873, filed Oct. 3, 2008.
U.S. Appl. No. 12/246,553, filed Oct. 7, 2008.
U.S. Appl. No. 12/248,115, filed Oct. 9, 2008.
U.S. Appl. No. 12/353,474, filed Jan. 14, 2009.
U.S. Appl. No. 12/353,470, filed Jan. 14, 2009.
U.S. Appl. No. 12/352,942, filed Jan. 13, 2009.
U.S. Appl. No. 12/237,556, filed Sep. 25, 2008.
U.S. Appl. No. 12/411,542, filed Mar. 26, 2009.
U.S. Appl. No. 12/248,104, filed Oct. 9, 2008.
U.S. Appl. No. 12/254,123, filed Oct. 20, 2008.
U.S. Appl. No. 12/200,246, filed Aug. 28, 2008.
U.S. Appl. No. 12/200,396, filed Aug. 28, 2008.
U.S. Appl. No. 12/200,526, filed Aug. 28, 2008.
U.S. Appl. No. 12/236,666, filed Sep. 24, 2008.
U.S. Appl. No. 12/192,189, filed Aug. 15, 2008.
U.S. Appl. No. 12/192,243, filed Aug. 15, 2008.
U.S. Appl. No. 12/331,643, filed Dec. 10, 2008.
U.S. Appl. No. 12/353,466, filed Jan. 14, 2009.
U.S. Appl. No. 12/363,086, filed Jan. 30, 2009.
U.S. Appl. No. 12/419,729, filed Apr. 7, 2009.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.

Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Intl Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 152267.2 dated Jun. 15, 2009.
Int'l Search Report EP 09 152898.4 dated Jun. 10, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.

* cited by examiner

APPARATUS, SYSTEM, AND METHOD FOR PERFORMING AN ELECTROSURGICAL PROCEDURE

BACKGROUND

1. Technical Field

The present disclosure relates to an apparatus, system, and method for performing an electrosurgical procedure. More particularly, the present disclosure relates to an apparatus, system, and method for performing an electrosurgical procedure that employs an electrosurgical apparatus that includes an end effector assembly configured for use with various size access ports.

2. Description of Related Art

Electrosurgical apparatuses (e.g., electrosurgical forceps) are well known in the medical arts and typically include a handle, a shaft and an end effector assembly operatively coupled to a distal end of the shaft that is configured to manipulate tissue (e.g., grasp and seal tissue). Electrosurgical forceps utilize both mechanical clamping action and electrical energy to effect hemostasis by heating the tissue and blood vessels to coagulate, cauterize, seal, cut, desiccate, and/or fulgurate tissue As an alternative to open electrosurgical forceps for use with open surgical procedures, many modern surgeons use endoscopes and endoscopic electrosurgical apparatus (e.g., endoscopic forceps) or laparoscopes for remotely accessing organs through smaller, puncture-like incisions. As a direct result thereof, patients tend to benefit from less scarring and reduced healing time. Typically, a forceps are inserted into the patient through one or more various types of cannulas or access ports (typically having an opening that ranges from about five millimeters to about twelve millimeters) that has been made with a trocar; as can be appreciated, smaller cannulas are usually preferred.

Forceps that are configured for use with small cannulas (e.g., cannulas less than five millimeters) may present design challenges for a manufacturer of electrosurgical instruments.

SUMMARY

As noted above, smaller cannulas or access ports are usually preferred during an electrosurgical procedure. However, because of size constraints associated with the cannula or access port, forceps that are configured for use with the smaller cannulas may present design challenges for a manufacturer (e.g., designing an end effector assembly of an endoscopic forceps without compromising the integrity and/or functionality thereof).

Therefore, it may prove useful in the relevant arts to provide a forceps that includes an end effector assembly that is configured for use with various types of cannulas or access ports including those that are less than five millimeters. With this purpose in mind, the present disclosure provides a bipolar forceps including a housing having a shaft that extends therefrom and defines a longitudinal axis therethrough. The housing includes a drive assembly disposed therein and operable to reciprocate an actuation tube within the shaft. The shaft includes an electrically conductive distal in. The actuation tube is configured to conduct current. An end effector assembly operatively connects to an electrically conductive distal end of the shaft. The end effector assembly includes a pair of first and second jaw members biased in an open configuration. Each of the first and second jaw members is pivotable about a living hinge. Distal reciprocation of the actuation tube causes each of the jaw members towards one another about the living hinge. In embodiments, one of the jaw members is in electrical communication with the distal end of the shaft and the other jaw member is in selective electrical communication with a distal end of the actuation tube such that when the jaw members are in a closed configuration a closed loop electrical circuit is formed.

BRIEF DESCRIPTION OF THE DRAWING

Various embodiments of the present disclosure are described hereinbelow with references to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

As noted above, it may prove useful in the arts to provide an electrosurgical apparatus that is suitable for use with various access ports, including but not limited to those that are greater than and/or less than five millimeters. With this purpose in mind, the present disclosure includes an electrosurgical forceps that includes an actuation tube that includes conductive and non-conductive portions each operatively coupled to one or more jaw members associated with the end effector assembly of the electrosurgical forceps. The actuation tube configured to move the jaws from an open to a closed configuration that forms a closed loop electrical circuit such that a desired tissue effect (e.g., tissue seal) may be achieved.

Figure 1:
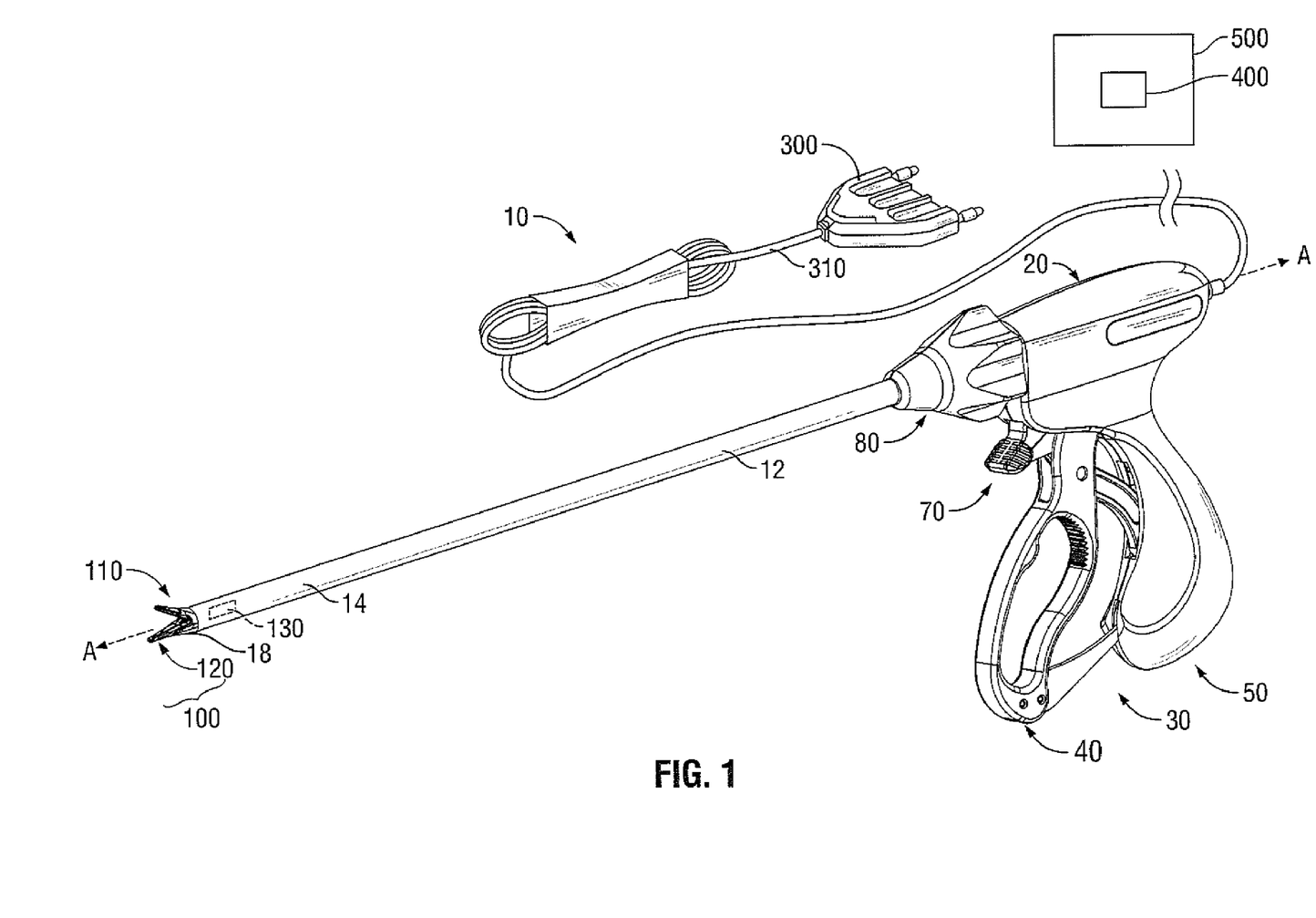
FIG. 1 is a perspective view of an laparoscopic bipolar forceps including an end effector assembly, and electrosurgical generator in accordance with an embodiment of the present disclosure.

With reference to FIG. 1 an illustrative embodiment of an electrosurgical apparatus (e.g., bipolar forceps 10) for performing an electrosurgical procedure is shown. Bipolar forceps 10 is operatively and selectively coupled to an electrosurgical generator (generator 500) for performing an electrosurgical procedure. As noted above, an electrosurgical procedure may include sealing, cutting, cauterizing coagulating, desiccating, and fulgurating tissue; all of which may employ RF energy. Generator 500 may be configured for monopolar and/or bipolar modes of operation. Generator 200 may include or is in operative communication with a system (system 400) that may include one or more processors in operative communication with one or more control modules that are executable on the processor. A control module (not explicitly shown) instructs one or more modules to transmit electrosurgical energy, which may be in the form of a wave or signal/pulse, via one or more cables (e.g., cable 310) to one or both of the seal plates 118, 128. For a more detailed description of the generator 500 and/or system 400 reference is made to commonly owned U.S. application Ser. No. 10/427,832.

Figure 3:
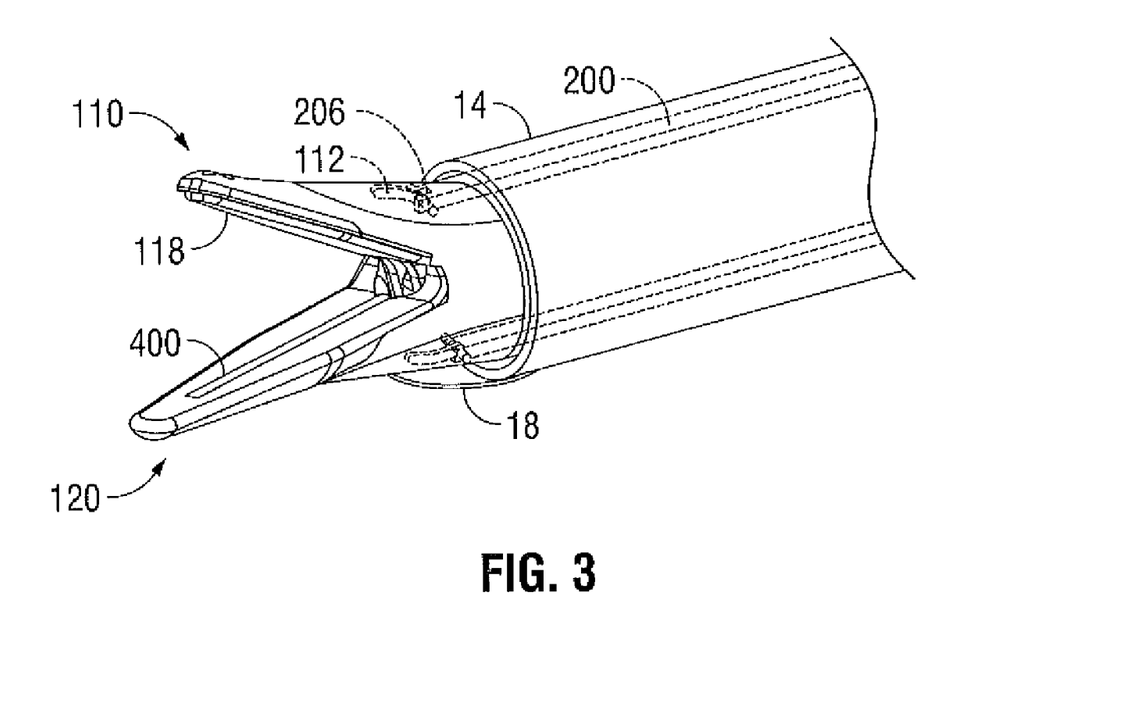
FIG. 3 is an enlarged, side view of the end effector assembly of FIG. 1.
Figure 4A:
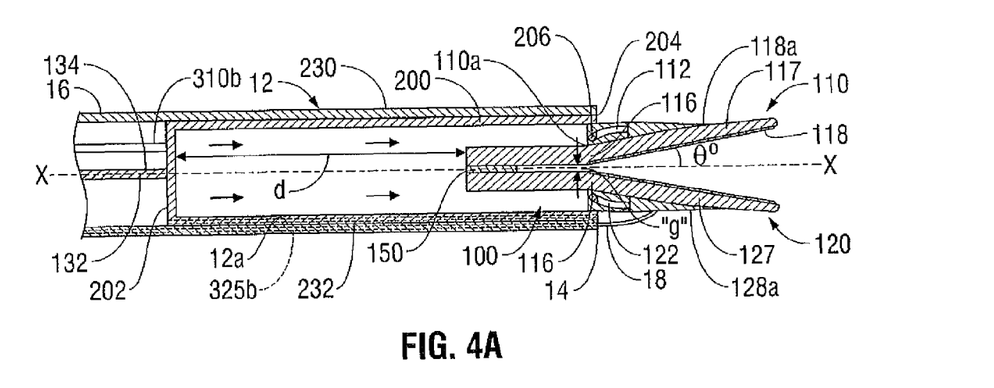
FIGS. 4A-4C are side, perspective views of an actuation rod configuration for use with the end effector assembly depicted in FIG. 1 in accordance with an embodiment of the present disclosure.
Figure 4B:
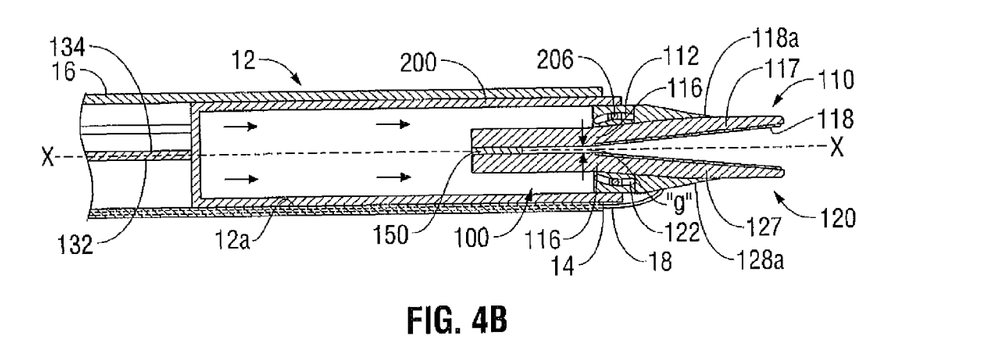
Figure 4C:
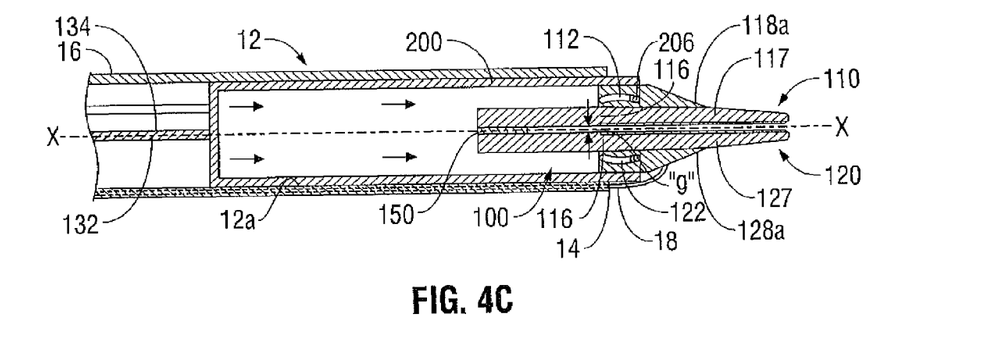

With continued reference to FIG. 1, bipolar forceps 10 is shown for use with various electrosurgical procedures and generally includes a housing 20, a handle assembly 30, a rotating assembly 80, a trigger assembly 70, a drive assembly 130, and an end effector assembly 100, which operatively connects to the drive assembly 130 via an actuation tube 200 (see FIGS. 3-4C). End effector assembly 100 includes opposing jaw members 110 and 120, which mutually cooperate to grasp, seal and, in some cases, divide large tubular vessels and large vascular tissues (FIG. 1). Although the majority of the figure drawings depict a bipolar forceps 10 for use in connection with laparoscopic surgical procedures, the present disclosure may be used for more traditional open surgical procedures or endoscopic procedures. For the purposes herein, the forceps 10 is described in terms of an laparoscopic instrument; however, an open version of the forceps may also include the same or similar operating components and features as described below.

Forceps 10 includes a shaft 12, as described in greater detail below with reference to FIG. 3, which has a distal end 14 configured in such a manner that a drive rod 132 of drive assembly 130 mechanically engages the end effector assembly 100 and a proximal end 16 which mechanically engages the housing 20. In the drawings and in the descriptions that follow, the term "proximal," as is traditional, will refer to the end of the forceps 10 that is closer to the user, while the term "distal" will refer to the end that is farther from the user.

With continued reference to FIG. 1, handle assembly 30 includes a fixed handle 50 and a movable handle 40. Fixed handle 50 is integrally associated with housing 20 and handle 40 is movable relative to fixed handle 50. Fixed handle 50 may include one or more ergonomic enhancing elements to facilitate handling, e.g., scallops, protuberances, elastomeric material, etc.

Movable handle 40 of handle assembly 30 is operatively connected to drive assembly 130 including drive rod 132, which together mechanically cooperate to impart movement of actuation tube 200. Movement of actuation tube 200 causes jaw members 110 and 120 to move from an open position, wherein the jaw members 110 and 120 are disposed in spaced relation relative to one another, to a clamping or closed position, wherein the jaw members 110 and 120 cooperate to grasp tissue therebetween.

Rotating assembly 80 is operatively associated with the housing 20 and is rotatable approximately 180 degrees about a longitudinal axis "A-A" defined through shaft 12 (see FIG. 1).

Figure 2:
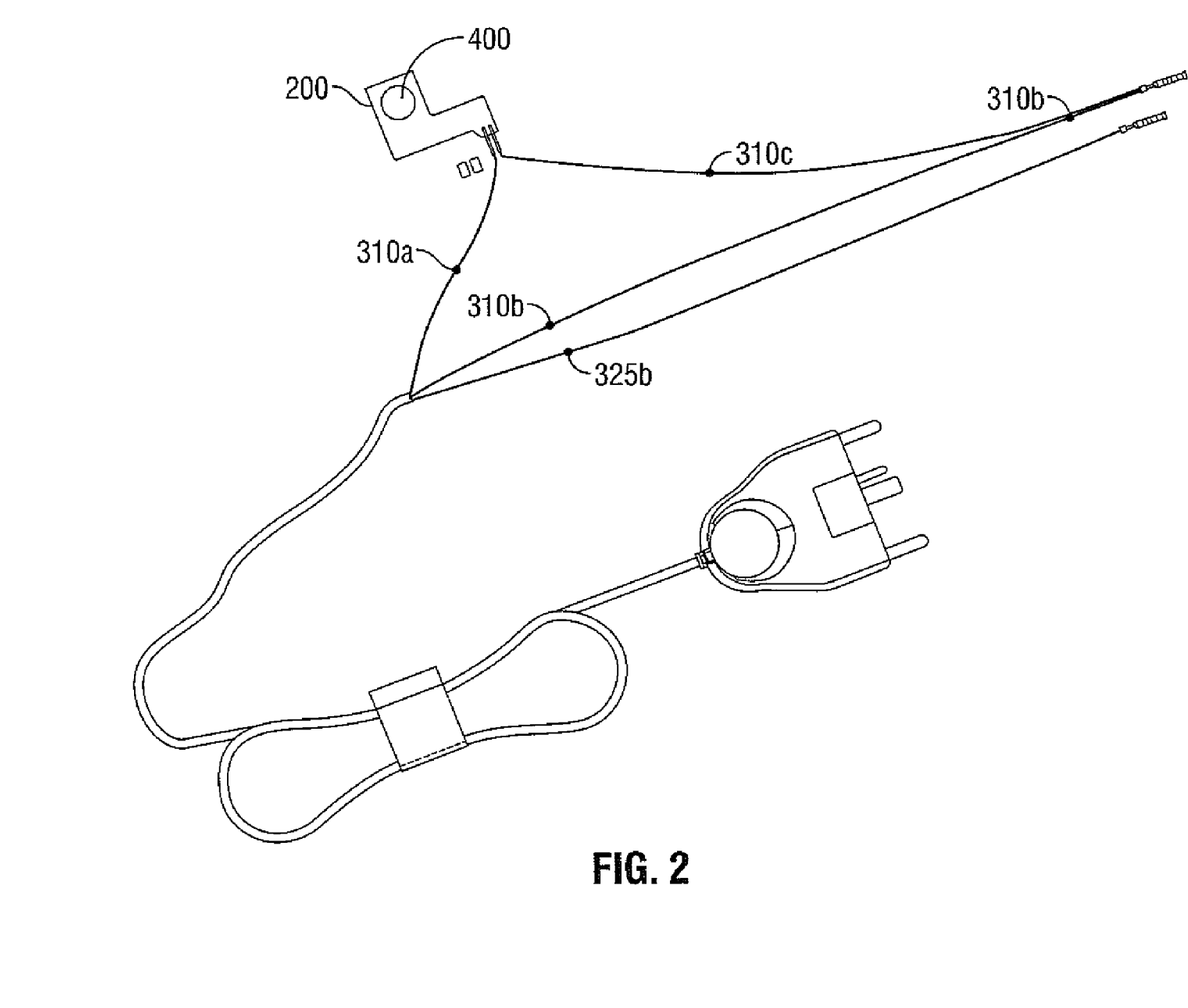
FIG. 2 is a schematic representation of an electrical configuration for connecting the bipolar forceps to the electrosurgical generator depicted in FIG. 1.

Forceps 10 also includes an electrosurgical cable 310 that connects the forceps 10 to a source of electrosurgical energy, e.g., generator 500. Cable 310 is internally divided into cable leads 310a, 310b, 310c, and 325b (see FIG. 2 for example) which are designed to transmit electrical potentials through their respective feed paths through the forceps 10 to the end effector assembly 100. More particularly, cable feed 325b connects through the forceps housing 20 and through the rotating assembly to one of the jaw members 110, 120, shaft 12, and/or the actuation tube 200, or portions thereof. Lead 310a connects to one side of a switch (not shown) and lead 310c connects to the opposite side of the switch such that upon activation of the switch energy is transmitted from lead 310a to 310c. Lead 310c is spliced with lead 310b which connects through the rotating assembly to jaw member 110, shaft 12, and/or the actuation tube 200, or portions thereof.

For a more detailed description of handle assembly 30, movable handle 40, rotating assembly 80, electrosurgical cable 310 (including line-feed configurations and/or connections), and drive assembly 130 reference is made to commonly owned U.S. application Ser. No. 10/369,894.

Turning now to FIG. 3, shaft 12 includes distal end 14 operatively connected to end effector assembly 100 and actuation tube 200. Shaft 12 is configured to house drive assembly 130 and actuation tube 200 or portions thereof. At distal end 14 of shaft 12, jaw members 110 and 120, or portions thereof, are attached to an inner surface 12a (FIG. 4A) of shaft 12 via any suitable attaching means including but not limited to staking, welding, riveting, molding or overmolding.

Distal end 14 of shaft 12 is in electrical communication with one or both of the jaw members 110, 120 (e.g., jaw 120) and configured to provide a path for current flow when the jaw members 110, 120 are in a closed configuration. With this purpose in mind, distal end 14 of shaft 12 includes one or more suitable conductive elements 18. An electrical contact 18 (contact 18) is operatively coupled to distal end 14 of shaft 12 and supported thereon. Contact 18 may any suitable electrical contact. For example, contact 18 may be in the form of an electrical brush of the type employed for use with commutators associated with motors and generators. A spring (not explicitly shown) may be employed with the contact 18, to maintain the contact 18 in constant electrical communication with one or both of the jaw members 110, 120 (e.g., jaw 120). Contact 18 is in electrical communication with generator 400 by way of, for example, lead 325b that extends to the distal end 14 of shaft 12 (see FIG. 4A for example). Contact 18 is also in electrical communication with one or both of the jaw members 110, 120 (e.g., 120, see FIG. 4A for example). Distal end 14 of shaft 12 is configured to support or provide a line-feed path for a portion of lead 325b (see FIG. 4A, for example). This support or feed path may be provided by a groove (not explicitly shown) that extends along a length of an outer or inner surface of shaft 12 at the distal end 14 thereof. Likewise, actuation tube 200, or portion thereof, may also be configured to support or provide a line-feed path for a portion of lead 325b (FIG. 4A for example).

Distal end 14 of shaft 12 is adapted to reciprocate actuation tube 200. Additionally, distal end 14 is dimensioned to allow jaw members 110 and 120 to flex, from an opened to closed configuration, during translation of actuation tube 200.

With continued reference to FIGS. 4A, actuation tube 200 is shown. Actuation tube 200 may be manufactured from any suitable material including but not limited to plastics, metals, and the likes, or combinations thereof. Actuation tube 200 may have any suitable geometric shape. In the illustrated embodiment, actuation tube 200 includes a proximal end 202 and a distal end 204 defining a generally cylindrical structure, which includes one or more cam pins 206 (two cam pins 206 shown). Actuation tube 200 is configured for longitudinal translation with respect to each of jaw members 110 and 120, and a non-conductive spacer 150.

In embodiments, actuation tube 200 includes a conductive portion 230 that is in electrical communication with or more electrical leads (e.g., lead 310b), and a non-conductive portion 232. Conductive portion 230 is configured to contact one or more of the jaw members 110, 120 (e.g., jaw 110) when the jaw members are in a closed configuration. This contact between the conductive portion 230 and the jaw member 110 in combination with jaw member 120 in contact with contact 18, close a loop of an electrical circuit which gives a return path for the current to flow back to the generator 500.

In some embodiments, and as noted above, non-conductive portion 232 may be configured to support or provide a line-feed path for one or more electrical leads (e.g., 325b) that is in electrical communication with contact 18 (see FIG. 4A, for example). However, in this instance, contact 18 may be operatively supported on distal end 204 of actuation.

Actuation tube 200 is configured to fit within shaft 12, such that when drive rod 132 of drive assembly 130 is translated or "pushed" in a distal direction, cam pins 206 of actuation tube 200 ride along a corresponding number of cam slots 112 and 122 located on the jaw members 110 and 120, respectively.

More particularly, proximal end 202 of actuation tube 200 is operatively connected to distal end 134 of drive rod 132, set back approximately a distance "d" from a proximal end of jaw members 110 and 120. A distal end 204 of actuation tube 200 is operatively connected to, and in mechanical communication with, one or more of the jaw members 110, 120 (both jaw members 110 and 120 are shown in mechanical communication with distal end 204). The distances that proximal end 202 of actuation tube 200 and distal end 134 of drive rod 132 may be set back from the proximal end of spacer 150 may vary. For example, distance "d" may be a distance that allows actuation tube 200 to translate distally and cause jaw members 110 and 120 to go from an open configuration to a closed configuration.

Distal end 204, or a portion thereof, of actuation tube 200 is configured for translation within shaft 12. Distal end 204 is operatively connected to one or more of cam slots 112 and 122 of jaw members 110 and 120, respectively, via mechanical engagement between one or more cam pins 206 (two cam pins 206 are shown).

Cam pins 206 extend laterally from an inside surface of actuation tube 200 and are configured to mechanically communicate with cam slots 112 and 122 to move the jaw members 110 and 120 from the open (FIG. 4A) to closed (FIG. 4C) configurations. Because jaw members 110 and 120 are in electrical communication with a source of electrosurgical energy, it may be useful to have cam pin 206, or portion thereof, manufactured from a non-conductive material. Cam pin 206 may be biased in a direction that is normal to the longitudinal axis "X". Biasing cam pins 206 in such a manner may facilitate closing the jaw members 110, 120.

With reference again to FIG. 4A, jaw member 110 includes an insulative jaw housing 117 and an electrically conductive seal plate 118 (hereinafter seal plate 118). The insulator 117 is configured to securely engage the electrically conductive seal plate 118. This may be accomplished by stamping, by overmolding, by overmolding a stamped electrically conductive sealing plate and/or by overmolding a metal injection molded seal plate. All of these manufacturing techniques produce an electrode having a seal plate 118 that is substantially surrounded by the insulating substrate. Within the purview of the present disclosure, jaw member 110 may include a jaw housing 117 that is integrally formed with a seal plate 118.

Jaw member 120 includes a similar structure having an outer insulative housing 127 that is overmolded to capture seal plate 128.

Jaw member 110 includes a living hinge 116 located at a proximal end 110a thereof. Proximal end 110a of jaw member 110 is bent near a distal end of spacer 150, such that a living hinge 116 is formed. Hinge 116 is bent in such a manner that an angle θ is formed relative to the longitudinal axis "X", as best seen in FIGS. 3 and 4A. The angle θ may range from about 0° to about 90°. Other angles θ of the jaw member 110 relative to the longitudinal axis "X" are contemplated and within the scope of the present disclosure.

Each of the jaw members 110, 120 include a respective outer conductive surface 118a, 128a configured to provide a path for current flow when the jaw members 110, 120 are in a closed configuration such that a desired tissue effect may be achieved. With this purpose in mind, outer conductive surfaces 118a, 128a are in electrical communication with respective seal plates 118, 128. In the embodiments illustrated in FIGS. 4A-4C, outer conductive surface 118a of jaw 110 contacts outer conductive portion 230 of actuation tube 200 when the jaw members 110, 120 are in a closed configuration, and conductive surface 128a of jaw member 120 and electrical contact 18 are maintained in electrical communication, for example, by way of a spring.

Cam slot 112 is located on a surface of jaw member 110 and interacts with cam pin 206 of actuation tube 200, as shown in FIGS. 4A-4C. Cam slot 112 may be formed on jaw member 110 by any of the previously described stamping and/or overmolding manufacturing techniques and may be formed by other suitable methods, e.g., drilling, etching, or machining, and so on. Cam slot 112 is configured in a manner such that when cam pin 206 rides along cam slot 112, jaw member 110 pivots about living hinge 116. While cam slot 112 is depicted as having a generally concave or arcuate structure, cam slot 112 may have any suitable structure that will allow jaw member 110 to function as described above. Cam slot 112 may be formed on a side surface (not explicitly shown), of jaw member 110. This, of course, will depend on the contemplated uses by the manufacturer.

Cam slot 122, operatively formed on jaw member 120, is configured in a manner that is the same as or substantially similar to cam slot 112 of jaw member 110.

Spacer 150 may be integrally formed with one or both of the jaw members 110 and 120, via any of the previously described manufacturing techniques, e.g., stamping and/or overmolding. Alternatively, spacer 150 may be a separate member operatively connected to each of the jaw members 110 and 120, or operatively connected to a distal end 14 of shaft 12. As mentioned above, spacer 150 may be configured to define a gap distance "g" between jaw members 110 and 120 (FIGS. 4A-4C). Gap distance may be any suitable distance; however, in one embodiment, gap distance "g" may be between about 0.001 inches and 0.006 inches. Gap distances less than 0.001 inches and greater than 0.006 inches are within the purview of the present disclosure. Spacer 150 is configured to isolate the electrically conductive seal surfaces 118 and 114 of jaw members 110 and 120, respectively. Spacer 150 may be formed from any suitable material including but not limited plastics, metals, and the like. Spacer 150 may be either conductive, non-conductive, or a combination thereof.

Spacer 150 may include a knife slot (not explicitly shown) defined therethrough configured to receive a knife blade, or portion thereof, and allow translation of the knife blade therethrough. The knife slot may extend distally from spacer 150 and substantially align with a knife slot 180 located on one or more of the jaw members 110 and 120 (FIG. 3)

In use, prior to sealing tissue, jaw members 110 and 120 initially may be biased in an open configuration, each disposed at an angle θ relative to the longitudinal axis like "X", and actuation tube 200 may be set back at a distance "d" from the proximal end of jaw member (FIG. 4A). When tissue is ready to be grasped for treating, a user positions tissue between jaw members 110 and 120, and squeezes handle 40 which, in turn, causes drive rod 132 of drive assembly 103 to translate distally. As drive rod 132 is translated or "pushed" distally, actuation tube 200 translates distally, which, in turn, causes cam pins 206 to ride along cam slots 112 and 122 of jaw members 110 and 120, respectively. As actuation tube 200 moves distally, jaw members 110 and 120 will flex radially inwardly, about living hinge 116, toward each other and the longitudinal axis "X" (FIG. 4B). When proximal end 202 of actuation tube 200 has moved approximately a distance "d", jaw members 110 and 120 will be substantially parallel to each other and the longitudinal axis "X", separated approximately by a gap distance "g" causing tissue to be grasped therebetween (FIG. 4C). After tissue is grasped between jaw members 110 and 120, electrosurgical energy may be transmitted by way of the electrical circuit formed by jaw members 110 and 120 and conductive portion 230 of actuation tube 200 and electrical contact 18, respectively, effecting a tissue seal therebetween, or other suitable tissue effect.

Upon completion of effecting a tissue seal, a user releases handle 40, which, in turn, causes drive rod 132 of drive rod assembly 130 to translate proximally. As drive rod 132 is translated or "pulled" distally, actuation tube 200 translates proximally, which, in turn, causes cam pins 206 to ride along cam slots 112 and 122 of jaw members 110 and 120, respectively. As actuation tube 200 moves proximally, jaw members 110 and 120 will flex radially outward, about living hinge 116, away from each other and the longitudinal axis "X" (FIG. 4B). When proximal end 202 of actuation tube 200 has moved approximately a distance "d", jaw members 110 and 120, returning to their initial open configuration, will again be disposed at an angle θ relative to the longitudinal axis "X" (FIG. 4A) and the electrical circuit formed by jaw members 110 and 120 and conductive portion 230 of actuation tube 200 and electrical contact 18, respectively, will be open, and, thus preventing the transmission of electrosurgical energy.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A bipolar forceps, comprising:
    a housing having a shaft that extends therefrom that defines a longitudinal axis therethrough, the shaft including an electrically conductive distal end, the housing including a drive assembly disposed therein, the drive assembly being operable to reciprocate an actuation tube within the shaft, at least a portion of the actuation tube being electrically conductive; and
    an end effector assembly operatively connected to the shaft and having a pair of first and second jaw members biased in an open configuration, each of the first and second jaw members being pivotable about a living hinge, wherein distal reciprocation of the actuation tube causes each of the jaw members towards one another about the living hinge,
    wherein one of the jaw members is in electrical communication with the distal end of the shaft and the other jaw member is in selective electrical communication with a distal end of the actuation tube such that when the jaw members are in a closed configuration a closed loop electrical circuit is formed.

2. The bipolar forceps according to claim 1, wherein the jaw members are electrically isolated from each other via a non-conductive spacer disposed at a proximal end therebetween.

3. The bipolar forceps according to claim 1, wherein the distal end of the shaft includes an electrically conductive member that contacts at least a portion of one of the first and second jaw member that is not in electrical communication with the actuation tube.

4. The bipolar forceps according to claim 3, wherein the electrically conductive member is a brush contact.

5. The bipolar forceps according to claim 1, wherein the actuation tube is in electrical communication with at least one electrical lead in electrical communication with a source of electrical energy.

6. The bipolar forceps according to claim 1, wherein the actuation tube is made of an electrically conductive material.

7. The bipolar forceps according to claim 1, wherein at least a portion of the actuation tube is insulated.

8. The bipolar forceps according to claim 1, wherein the drive assembly includes an actuation rod coupled to the actuation tube to actuate the jaw members.

* * * * *